United States Patent [19]

D'Silva

[11] 4,166,864
[45] Sep. 4, 1979

[54] PESTICIDAL UNSYMMETRICAL BIS-ARYLCARBAMATE DISULFIDE COMPOUNDS

[75] Inventor: Themistocles D. J. D'Silva, South Charleston, W. Va.

[73] Assignee: Union Carbide Corporation, New York, N.Y.

[21] Appl. No.: 781,986

[22] Filed: Mar. 28, 1977

[51] Int. Cl.$^2$ .................... A01N 9/28; C07D 307/86; A01N 9/12; C07C 125/06
[52] U.S. Cl. .................................. 424/285; 424/275; 424/276; 424/277; 424/278; 424/282; 424/283; 424/300; 260/340.3; 260/340.5 R; 260/340.7; 260/340.6; 549/30; 549/39; 549/51; 260/340.9; 260/346.73; 260/465 D; 560/29; 560/134; 560/135; 560/136; 560/137; 560/148

[58] Field of Search ................ 260/327, 330.5, 340.3, 260/340.5, 340.6, 340.7, 340.9, 346.73, 465 D; 424/275, 276, 277, 278, 282, 285, 283, 300; 560/29, 134, 135, 136, 137, 148

[56] References Cited

U.S. PATENT DOCUMENTS 3,857,860  12/1974  Kuhle et al. .................... 560/135

FOREIGN PATENT DOCUMENTS 2131399  12/1972  Fed. Rep. of Germany.

*Primary Examiner*—Henry R. Jiles
*Assistant Examiner*—Bernard Dentz
*Attorney, Agent, or Firm*—Robert C. Brown

[57] ABSTRACT

Unsymmetrical bis-arylcarbamate disulfide compounds exhibit outstanding miticidal and insecticidal activity, coupled with substantially reduced mammalian toxicity and phytotoxicity as compared to known pesticidal compounds having a comparable spectrum of activity against insect and mite pests.

26 Claims, No Drawings

PESTICIDAL UNSYMMETRICAL BIS-ARYLCARBAMATE DISULFIDE COMPOUNDS

This invention relates to unsymmetrical bis-arylcarbamate disulfide compounds and to methods for preparing the same. This invention is also directed to insecticidal, miticidal and nematocidal compositions comprising an acceptable carrier and insecticidally, miticidally or nematocidally effective amount of a compound according to this invention as well as to a method of controlling insects, mites and nematodes by subjecting them to an insecticidally, miticidally or nematocidally effective amount of a compound of this invention.

More particularly, this invention relates to compounds of the formula:

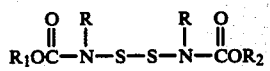

wherein:
R is alkyl having from 1 to 4 carbon atoms;
$R_1$ and $R_2$ are different and are individually naphthyl, tetrahydronaphthyl, dihydrobenzofuranyl, benzofuranyl, benzodioxanyl, methylenedioxyphenyl, benzodioxalanyl, benzothienyl or indanyl all of which may be either unsubstituted or substituted with one or more alkyl groups; or either substituted or unsubstituted phenyl wherein the permissible substituents are one or more alkyl, alkenyl, alkynyl, alkoxycarbonylamino, alkoxy, alkynyloxy, phenoxy, alkylsulfinyl, alkylsulfonyl, alkylthio, alkenylthio, dialkylaminoalkyleneamino, alkynylthio, alkylthioalkyl, alkylsulfinylalkyl, alkylsulfonylalkyl, amino, alkylamino, dialkylamino, trihalomethyl, halo, nitro, cyano, cycloalkyl, formamidino, 2-dioxanyl, 2-dioxolanyl, 2-dithiolanyl, 2-oxathiolanyl or dicyanoethenylene;

With the proviso that $R_1$ and $R_2$ substituents individually may not include more than eight aliphatic carbon atoms.

The formamidino and the dialkylamino substituents can also be in the form of the salts of organic or inorganic acid, as for example, the oxalate, citrate, acetate, propionate, chloride, phosphate, nitrate, sulfonate, sulfate, chlorate or formate salt.

The following miticidally, insecticidally, and nematicidally active compounds are illustrative of the compounds of this invention simply by selecting appropriate starting materials for use in the procedures described below:

N-[2,2-Dimethyl-2,3-dihydro-7-benzofuranylmethylcarbamate]
N-[3-(1-methylpropyl)phenyl methylcarbamate]disulfide
N-[2,2-Dimethyl-2,3-dihydro-7-benzofuranyl methylcarbamate]
N-[4-dimethylamino-3,5-xylyl methylcarbamate]disulfide
N-[2,2-Dimethyl-2,3-dihydro-7-benzofuranyl methylcarbamate]
N-[2,2-dimethylbenzodioxanyl-4-methylcarbamate]disulfide
N-[1-Naphthylmethylcarbamate] N-[3,4-methylenedioxyphenyl methylcarbamate]disulfide
N-[1-Naphthylmethylcarbamate] N-[4-methylthio-3,5-xylyl methy,carbamate]disulfide
N-[Naphthylmethylcarbamate] N-[3,5-xylyl methylcarbamate]disulfide
N-[1-Naphthylmethylcarbamate] N-[3,5-disopropylphenylmethylcarbamate]disulfide
N-[1-Naphthylmathylcarbamate] N-[2-ethylthiomethylphenylmethylcarbamate]disulfide
N-[1-Naphthylmethylcarbamate] N-[4-benzothienylmethylcarbamate]disulfide
N-[1-Naphthylmethylcarbamate] N-[4-dimethylaminomethyleneimino-3,5-xylyl methylcarbamate]disulfide
N-[1-Naphthyl methylcarbamate] N-[4-dimethylaminomethyleneimino-3-isopropylphenyl methylcarbamate]disulfide, hydrochloride
N-[1-Naphthyl methylcarbamate] N-[4-(2,2-dicyanoethenylene) 2,6-di-tert-butylphenyl methylcarbamate]disulfide
N-[1-Naphthyl methylcarbamate] N-[3-dimethylaminophenyl methylcarbamate]disulfide hydrochloride
N-[2-Methyl-2,3-dihydro-7-benzofuranyl methylcarbamate] N-[3-trifluoromethylphenyl methylcarbamate]disulfide
N-[1-Naphthyl methylcarbamate] N-[3-dimethylaminomethyleneiminophenyl methylcarbamate]disulfide oxalate
N-[2,2-Dimethyl-2,3-dihydro-7-benzofuranyl methylcarbamate] N-[2-chlorophenyl methylcarbamate]disulfide
N-[2,2-Dimethyl-2,3-dihydro-7-benzofuranyl methylcarbamate] N-[4-(dimethylaminomethyleneimino)-3-methylphenyl methylcarbamate]-disulfide hydrochloride
N-[2-(1,3-oxathiolan-2-yl)phenyl methylcarbamate] N-[3-ethynylphenyl methylcarbamate]disulfide
N-[2-(1,3-dioxolan-2-yl)phenyl methylcarbamate] N-[4-cyanophenyl methylcarbamate]disulfide
N-[3,4-Methylenedioxyphenyl methylcarbamate] N-[2-cyclopropylphenyl methylcarbamate]disulfide
N-[5,6,7,8-Tetrahydronaphthyl methylcarbamate] N-[4-methylsulfinyl-3,5-xylyl methylcarbamate]disulfide
N-[2-Isopropylphenyl methylcarbamate] N-[3-phenoxyphenyl methylcarbamate]disulfide
N-[1-Naphthyl methylcarbamate] N-[2-(dithiolan-2-yl) phenyl methylcarbamate]disulfide
N-[1-Naphthyl hexylcarbamate] N-[2-oxathiolan-2-yl)phenyl hexylcarb mate]disulfide
N-[1-Naphthyl methylcarbamate] N-[2-isopropoxyphenyl carbamate]disulfide
N-[3-Isopropylphenylmethylcarbamate] N-[2,3-dihydro-2, 2-dimethyl-7-benzofuranyl methylcarbamate]disulfide.

All of the compounds within the purview of the generic formula set forth above exhibit nematicidal, miticidal and insecticidal activity to a lesser or greater extent. Accordingly, these compounds are useful for the control of mite, nematode and insect pests. Some of the compounds of this invention exhibit excellent levels of nematocidal, miticidal and insecticidal activity in extremely small dosages while others require larger dosages to be effective. They also exhibit excellent leaf and soil residual activity.

In general, the compounds of this invention are either totally lacking in phytotoxicity or exhibit only minimal phytotoxicity with respect to economically important crop species. In addition, these compounds exhibit substantially reduced levels of mammalian toxicity as compared to known pesticidal compounds having a comparable spectrum of activity against insect, arachnid and nematode pests.

Preferred because of their higher levels of miticidal, insecticidal and nematocidal activity are the compounds of this invention in which:

R is methyl;

wherein:

R$_1$ and R$_2$ are different and are naphthyl, tetrahydronaphthyl, dihydrobenzofuranyl substituted with one or more alkyl, methylenedioxyphenyl, dihydrobenzofuranyl or either unsubstituted or substituted phenyl wherein the permissible substituents are one or more alkyl, alkylthio, alkylsulfonyl, alkylsulfinyl, alkynyloxy, alkoxy, 2-(1,3-dithiolan-2-yl), or dialkylamino.

Particularly preferred compounds of this invention are those wherein:

R is methyl;

R$_1$ and R$_2$ are different and are dihydrobenzofuranyl, naphthyl or phenyl substituted with one or more alkyl or dialkylamino groups.

The unsymmetrical bis-arylcarbamate compounds of this invention can be prepared by a variety of methods. One preferred method is illustrated be the reaction scheme set forth below in which R, R$_1$ and R$_2$ are described above:

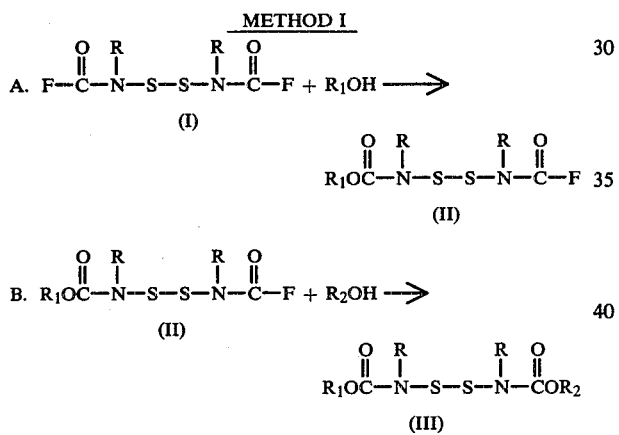

METHOD I is a two-step reaction sequence which can be conducted either in-situ or the carbamate-sulfenyl carbamoyl halide intermediate (II) of Step A can be isolated and used as the reactant of Step B at some latter time. In Step A, one equivalent of an appropriately substituted hydroxyl reactant, either R$_1$OH or R$_2$OH, is reacted with one equivalent of the bis-(N-alkyl-N-fluorocarbonylamino)disulfide reactant (I), in presence of at least one equivalent of an acid acceptor, preferably in an aprotic solvent to yield the intermediate carbamate sulfenyl carbamoyl halide (II). In Step B, an equivalent of the intermediate carbamate sulfenyl carbamoyl halide (II) reactant of Step A is then reacted with a second equivalent of a hydroxyl reactant, R$_1$OH if R$_2$OH was used as the reactant in step A or R$_2$OH if R$_1$OH was used as the reactant in step A. Step B is also conducted in the presence of at least one equivalent of an appropriate acid acceptor and in an aprotic solvent, to yield the desired unsymmetrical bis-carbamate compound (III).

Normally an aprotic organic solvent is employed as the reaction medium. Illustrative of aprotic organic solvents which are suitable as reaction solvents in the practice of the preferred embodiments of this invention are saturated and unsaturated aliphatic and aromatic hydrocarbons, e.g. hexane, cyclohexane, octane, dodecane, naphtha, decalin, kerosene, tetrahydronapthalnen, cycloheptane, alkylcycloalkane, benzene, toluene, xylene, naphthalene, alkylnaphthalene, or the like, ethers such as tetrahydrofuran, tetrahydropyran, diethyl ether, dioxane, 1,2-dimethoxybenzene, 1,2-ethoxybenzene, the mono and dialkyl ethers of ethylene glycol, of dipropylene glycol, of butylene glycol, or diethylene glycol, of dipropylene glycol, or chlorinated aliphatic hydrocarbons as for example, chloroform, dichloromethane, methylene dichloride, 1,1-dichloroethane, carbon tetrachloride or the like.

The acid acceptor utilized in the conduct of the reaction of METHOD I may be either an organic or inorganic base. Illustrative of organic bases that are useful as acid acceptors are tertiary amines, alkali metal alkoxides or the like. Bases such as sodium hydroxide, potassium hydroxide or the like are illustrative of inorganic bases which are useful in the conduct of this reaction. Preferred acid acceptors are aromatic and aliphatic tertiary amines, such as triethylamine, pyridine, trimethylamine, 1,4-diazobicyclo[2.2.2]octane and the like.

When an inorganic base is used as the acid acceptor, phase transfer agents may be used to facilitate the transfer of the acid acceptor across the organic/inorganic phase interface. Illustrative of useful phase transfer agents are crown ether compounds, quaternary ammonium halide compounds or the like.

The reaction temperature is not critical and can be varied over a wide range. The reaction is preferably conducted at a temperature of from about $-30°$ C. and upwards to approximately $130°$ C. Particularly preferred reaction temperatures are from about $0°$ C. to about $75°$ C.

Reaction pressures are not critical. The process can be conducted at either subatmospheric, atmospheric or superatmospheric pressure. For convenience the reaction is usually conducted at atmospheric or autogeneous pressure.

Hydroxylated aryl compounds employed as reactants in the reaction of METHOD I are well known compounds that can be prepared by well known synthetic procedures or obtained from commercial sources.

The bis-(N-alkyl-N-fluorocarbonylamino)disulfide precursors can be conveniently prepared by reacting sulfur monochloride with N-alkylcarbamoyl fluoride in toluene in the presence of an acid acceptor as for example triethylamine or pyridine. This procedure is described in more detail in U.S. Pat. No. 3,639,471.

The following specific examples are presented to particularly illustrate the invention:

EXAMPLE I

Preparation of 7-[N-Methyl-N-(N'-methyl-N'-fluoroformyl aminothiosulfenyl)carbamoyloxy]-2,3-dihydro 2,2-dimethyl benzofuran 7-[N-Methyl-N-(N'-methyl-N'-fluoroformylaminothiosulfenyl)carbamoyloxy]-2,3-dihydro-2,2-dimethylbenzofuran was prepared by reacting 12.0 g (0.0731 m) of 2,3-dihydro-2,2-dimethyl-7-benzofuranol with 15.81 g of bis-(N-methyl-N-fluorocarbonylamino)disulfide and 7.40 g (0.0731 m) of triethylamine in 300 ml of toluene. The conventional work-up afforded 27.55 g of 7-[N-methyl-N-(N'-methyl-N'-fluoroformylaminothiosulfenyl)carbamoyloxy]-2,3-dihydro-2,2-dimethylbenzofuran as a reddish brown oil.

Calc'd. for $C_{14}H_{17}FN_2O_4S_2$: C, 46.65; H, 4.76; N, 7.77; Found: C, 46.85; H, 4.44; N, 7.84.

EXAMPLE II

Preparation of 4-tert-butylphenyl-N-methyl-N-(N'-methyl-N'-fluoroformylaminothiosulfenyl)carbamate Utilizing the procedure of Example I, 020.0 g (0.133 m) of p-tert-butylphenol was reacted with 28.77 g (0.133 m) of bis-(N-methyl-N-fluorocarbonylamino)disulfide and 13.46 g (0.133 m) of triethylamine in 300 ml of toluene. After stirring at ambient temperature for approximately 20 hrs. the reaction mixture was washed dilute sodium hydroxide solution and water. The usual work-up afforded 42.6 g of 4-tert-butylphenyl-N-methyl-N-(N'-methyl-N'-fluoroformylaminothiosulfenyl)-carbamate as an oil.

Calc'd for $C_{14}H_{19}FN_2O_3S_2$: C, 48.53; H, 5.53; N, 8.09; Found: C, 49.26; H, 5.31; N, 8.10.

EXAMPLE III

Preparation of N-[2,2-Dimethyl-2,3-dihydro-7-benzofuranyl methylcarbamate] N-[2-propargyloxyphenylmethylcarbamate]disulfide To a solution of 9.73 g (0.027 m) of 7-[N-methyl-N-(N'-methyl-N'-fluorocarbonylaminothiosulfenyl)carbamoyloxy]-2,3-dihydro-2,2-dimethylbenzofuran and 4.0 g (0.027 m) of 2-propargyloxyphenol in 150 ml of toluene, was added 2.73 g (0.027 m) of triethylamine. The reaction mixture was stirred overnight at room temperature and for an additional 24 hrs. at 50° C. On cooling, the reaction mixture was washed sequentially with water, dilute sodium hydroxide solution and again with water until neutral. The organic layer was dried over magnesium sulfate and was concentrated under vacuum. An aliquot (5.0 g) of the crude oil was purified by column chromatography to afford 3.5 g of N-[2,2-Dimethyl-2,3-dihydro-7-benzofuranyl methyl carbamate] N-[2-propargyloxy phenylcarbamate]disulfide as a light yellow oil.

Calc'd for $C_{23}H_{24}N_2O_6S_2$: C, 56.54; H, 4.95; N, 5.74; Found: C, 56.37; H, 4.76; N, 5.60.

EXAMPLE IV

Preparation of N-[2,2-Dimethyl-2,3-dihydro-7-benzofuranyl methyl carbamate] N-[1-Naphthyl methylcarbamate]disulfide To a solution of 9.98 g (0.0277 m) of 7-[N-methyl-N-(N'-methyl-N'-fluorocarbonylaminothiosulfenyl) carbamoyloxy]-2,3-dihydro-2,2-dimethylbenzofuran and 4.0 g (0.0277 m) of 1-naphthol in 150 ml of toluene, was added with stirring 2.8 g (0.0277 m) of triethylamine. The reaction mixture was stirred for 24 hrs. at room temperature and for an additional 24 hrs. at 50° C. On cooling the mixture was washed with dilute sodium hydroxide solution followed by water wash until neutral. The organic layer was dried over magnesium sulfate and concentrated to afford 13.08 g of an oil. Purification by dry column chromatography afforded 3.56 g of N-[2,2-dimethyl-2,3-dihydro-7-benzofuranyl methyl carbamate] N-[1-naphthyl methylcarbamate]disulfide as a light brown amorphous solid.

Calc'd. for $C_{24}H_{24}N_2O_5S_2$: C, 59.48; H, 4.99; N, 5.78; Found: C, 59.25; H, 5.06; N, 5.64.

EXAMPLE V

Preparation of N-[2,2-Dimethyl-2,3-dihydro-7-benzofuranyl methylcarbamate] N-[3-methyl-4-methylthiophenylmethylcarbamate] disulfide To a solution of 4.0 g (0.026 m) of 3-methyl-4-methylthiophenol, and 9.34 g (0.026 m) of 7-[N-methyl-N-(N'-methyl-N'-fluorocarbonylaminothiosulfenyl)carbamoyloxy]-2,3-dihydro-2,2-dimethyl benzofuran in 150 ml of toluene, was added with stirring 3.10 g (0.0306 m) of triethylamine. The reaction mixture was heated at 40° C. for 48 hrs. On cooling the reaction mixture was washed with dilute sodium hydroxide solution followed by water wash. The organic layer was dried and concentrated to afford 12.57 g of a reddish brown oil which solidified on standing. Crystallization from isopropyl ether afforded 6.0 g of N-[2,2-dimethyl-2,3-dihydro-7-benzofuranyl methylcarbamate] N-[3-methyl-4-methylthiophenylcarbamate]disulfide as a white solid. m.p. 109°–111° C.

Calc'd. for $C_{22}H_{26}N_2O_5S_3$: C, 53.42; H, 5.30; N, 5.66; Found: C, 53.32; H, 5.16; N, 5.69.

EXAMPLE VI

Preparation N-[3,5-Dimethylphenylmethylcarbamate] [2,2-Dimethyl-2,3-dihydro-7-benzofuranyl methylmethylcarbamate]disulfide N-[3,5-Dimethylphenylmethylcarbamate] N-[2,2-dimethyl-2,3-dihydro-7-benzofuranyl methylcarbamate]disulfide was prepared according to the procedure employed in Example V by reacting 2.92 g of 3,5-dimethylphenol and 8.61 g of 7-[N-methyl N-(N'-methyl-N'-fluorocarbonylaminothiosulfenyl) carbamoyloxy]-2,3-dihydro-2,2-dimethylbenzofuran in 150 ml of toluene with 2.42 g of triethylamine. m.p. 118°–119.5° C.

Calculated for $C_{22}H_{26}N_2O_5S_2$: C, 57.12; H, 5.67; N, 6.06;

Found: C, 57.00; H, 5.69; N, 6.02.

EXAMPLE VII

Preparation of N-[3-Dimethylaminophenylmethylcarbamate] N-[2,2-Dimethyl-2,3-dihydro-7-benzofuranylmethylcarbamate] disulfide N-[3-Dimethylaminophenylmethylcarbamate] N-[2,2-dimethyl-2,3-dihydro-7-benzofuranyl methyl carbamate] disulfide was prepared according to the procedure employed in Example V by reacting 4.0 g of dimethylaminophenol and 10.52 g of 7-[N-methyl-N-(N'-methyl-N'-fluorocarbonylaminothiosulfenyl)carbamoyloxy]-2,3-dihydro-2,2-dimethylbenzofuran in 150 ml of toluene with 2.95 g of triethylamine. Weight of N-[3-Dimethylaminophenyl methyl carbamate] N-[2,2-Dimethyl-2,3-dihydro-7-benzofuranyl methylcarbamate]disulfide obtained was 13.9 g. The was purified by column chromatography.

Calculated for $C_{22}H_{27}N_3O_5S_2$: C, 55.32; H, 5.70; N, 8.80: Found: C, 54.28; H, 5.39; N, 8.35.

EXAMPLE VIII

Preparation of
N-[3,4-Methylenedioxyphenylmethylcarbamate]
N-[2,3-Dihydro-2,2-dimethyl-7-benzofuranylmethylcarbamate] disulfide N-[3,4-Methylenedioxyphenylmethylcarbamate] N-[2,3-dihydro-2,2-dimethyl-7-benzofuranylmethylcarbamate]disulfide was prepared according to the procedure employed in Example V, by reacting 2.07 g of 3,4-methylenedioxyphenol and 5.16 g of 7-[N-methyl-N-(N'-methyl-N'-fluorocarbonylaminothiosulfenyl)carbamoyloxy]-2,3-dihydro-2,2-dimethylbenzofuran in 75 ml of toluene with 1.52 g of triethylamine. The crude product (5.5 g) was purified by column chromatography to afford N-[3,4-Methylenedioxyphenylmethylcarbamate] N-[2,3-Dihydro-2,2-dimethyl-7-benzofuranylmethylcarbamate] disulfide as an oil.

Calculated for $C_{21}H_{22}N_2O_7S_2$: C, 52.70; H, 4.63; N, 5.86; Found: C, 50.89; H, 4.55; N, 5.61.

EXAMPLE IX

Preparation of
N-[2-(1,3-dithiolan-2-yl)-phenylmethylcarbamate]
N-[4-tert-butylphenylmethylcarbamate]disulfide N-[2-(1,3-dithiolan-2-yl)-phenylmethylcarbamate] N-[4-tert-butylphenylmethylcarbamate]disulfide was prepared essentially according to the procedure employed in Example III by reacting 2.97 g of 2-(1,3-dithiolan-2-yl) phenol and 5.19 g of 4-[N-methyl-N-(N'-methyl-N'-fluorocarbonylaminothiosulfenyl) carbamoyloxy]-tert-butylbenzene in 75 ml of toluene with 1.52 g of triethylamine. Crude N-[2-(1,3-dithiolan-2-yl)-phenylmethylcarbamate] N-[4-tert-butylphenyl carbamate] disulfide was purified by column chromatography.

Calculated for $C_{23}H_{28}N_2O_4S_4$: C, 52.64; H, 5.38; N, 5.34;

Found: C, 52.21; H, 5.52; N, 5.15.

Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (Aphis fabae Scop.) reared on potted dwarf nasturtium plants at 65°-70° C. and 50-70 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern arymworm (Prodenia eridania, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (Epilachna varivestis, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.) reared according to the specifications of the Chemical Specialties Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100=110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living. growing potted cucumber for approximately three weeks. These cucumber plants were then removed from the pots, the soil washed from the roots and the amount of galling visually rated.

In these tests the pesticidal activity of the compounds against aphid, mite, Southern Armyworm, Bean Beetle and house fly was rated as follows:
- A=excellent control
- B=partial control
- C=no control

Phytotoxicity Test

Experiments were also conducted to determine the phytotoxicity of representative compounds with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the foliage to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

The results of these experiments are also summarized in Table I below.

TABLE I

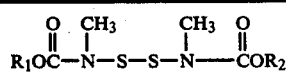

$$R_1OC(\!=\!O)\!-\!N(CH_3)\!-\!S\!-\!S\!-\!N(CH_3)\!-\!C(\!=\!O)OR_2$$

| | | BIOLOGICAL ACTIVITY | | | | | | | | | |
|---|---|---|---|---|---|---|---|---|---|---|---|
| | | Insecticidal And Miticidal | | | | | Phytotoxicity | | | | |
| R₁ | R₂ | Aphid | Mite | Southern Armyworm | Mexican Bean Beetle | Housefly | Bean | Corn | Tomato | Cotton | Soybean |
| 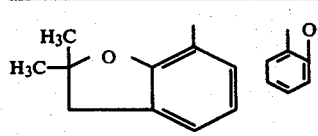 | O—CH₂C≡CH (phenyl) | A | C | A | A | A | 1 | 1 | 1 | 1 | 2 |

TABLE I-continued $$R_1OC(=O)-N(CH_3)-S-S-N(CH_3)-C(=O)OR_2$$

| | | BIOLOGICAL ACTIVITY | | | | | | | | | |
|---|---|---|---|---|---|---|---|---|---|---|---|
| | | Insecticidal And Miticidal | | | | | Phytotoxicity | | | | |
| $R_1$ | $R_2$ | Aphid | Mite | Southern Army-worm | Mexican Bean Beetle | House-fly | Bean | Corn | Tomato | Cotton | Soybean |
| 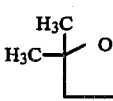 | 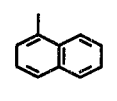 | A | C | A | A | A | 1 | 1 | 1 | 1 | 1 |
| 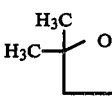 | 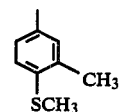 | A | C | A | A | A | 1 | 1 | 1 | 1 | 1 |
| 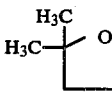 | 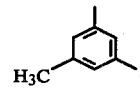 | A | C | A | A | A | 1 | 1 | 1 | 1 | 1 |
| 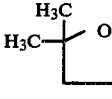 | 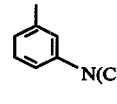 | A | C | A | A | A | 1 | 1 | 1 | 1 | 1 |
| 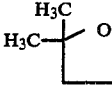 | 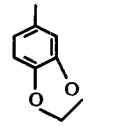 | A | C | A | A | A | 1 | 1 | 1 | 1 | 1 |
| 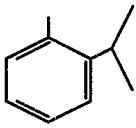 | 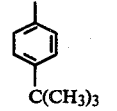 | A | C | C | A | A | 1 | 1 | 1 | 1 | 1 |

The pesticides contemplated herein prevent attack by insects, nematodes and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds. consistent with the desired dispersion of the toxicant in the spray so that rain does not re-emulsify the toxicant after it is applied to the plant and wash it off the plant. Nonionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre.

The results set forth in TABLE I clearly show the broad spectrum pesticidal activity of the compounds of this invention, as well as their reduced mammalian toxicity. It will be understood that the insect and mite species employed in the above tests are merely representative of a wide variety of pests that can be controlled through the use of the compounds of this invention.

The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible,

What is claimed is:

1. A compound of the formula:

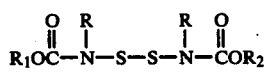

wherein:
R is alkyl having from 1 to 4 carbon atoms;
$R_1$ and $R_2$ are different and are naphthyl, tetrahydronaphthyl, dihydrobenzofuranyl, benzofuranyl, benzodioxanyl, methylenedioxyphenyl, benzothienyl or indanyl all of which may be either unsubstituted or substituted with one or more alkyl groups; or either unsubstituted or substituted phenyl, wherein the permissible substituents are one or more alkyl, alkenyl, alkynyl, alkoxy, alkynyloxy, phenoxy, alkylsulfonyl, alkylsulfinyl, alkylthio, alkenylthio,, alkoxycarbonylamino, dialkylaminoalkyleneamino, alkynylthio, alkylthioalkyl, alkylsulfinylalkyl, alkylsulfonylalkyl, amino, alkylamino, dialkylamino, trihalomethyl, halo, nitro, cyano, cycloalkyl, formamidino, 2-dioxanyl, 2-dioxolanyl, 2-dithiolanyl, 2-oxathiolanyl or dicyanoethenylene;
with the proviso that $R_1$ and $R_2$ substituents individually may not include more than eight aliphatic carbon atoms.

2. A compound according to claim 1 wherein R is methyl.

3. A compound according to claim 1 wherein $R_1$ and $R_2$ are different and are naphthyl, tetrahydronaphthyl, methylenedioxyphenyl, dihydrobenzofuranyl substituted with one or more alkyl, dihydrobenzofuranyl or either unsubstituted or substituted phenyl wherein the permissible substituents are one or more alkyl, alkylthio, alkylsulfinyl, alkylsulfonyl, alkoxy, alkynyoxy, 2-(1,3-dithiolan-2-yl) or dialkylamino.

4. A compound according to claim 1 wherein $R_1$ and $R_2$ are different and are dihydrobenzofuranyl, dihydrobenzofuranyl substituted with one or more alkyl, naphthyl or phenyl substituted with one or more alkyl or dialkylamino groups.

5. A compound according to claim 1 wherein:
R is methyl;
$R_1$ and $R_2$ are different and are naphthyl, tetrahydronaphthyl, methylenedioxyphenyl, dihydrobenzofuranyl substituted with one or more alkyl, dihydrobenzofuranyl or either unsubstituted or substituted phenyl wherein the permissible substituents are one or more alkyl, alkylthio, alkoxy, alkylsulfinyl, alkylsulfonyl, alkynyloxy, 2-(1,3-dithiolan-2-yl) or dialkylamino.

6. A compound according to claim 5 wherein $R_1$ and $R_2$ are different and are dihydrobenzofuranyl, naphthyl, dihydrobenzofuranyl substituted with one or more alkyl or phenyl substituted with one or more alkyl or dialkylamino groups.

7. N-[2,2-Dimethyl-2,3-dihydro-7-benzofuranylmethylcarbamate] N-[Naphthylmethylcarbamate]disulfide.

8. N-[3,5-Dimethylphenylmethylcarbamate] N-[2,2-Dimethyl-2,3-dihydro-7-benzofuranylmethylcarbamate]disulfide.

9. N-[3-Dimethylaminophenylmethylcarbamate] N-[2,2-Dimethyl-2,3-dihydro-7-benzofuranylmethylcarbamate]disulfide.

10. An insecticidal and miticidal composition comprising an acceptable carrier and as the active toxicant an insecticidally and miticidally effective amount of a compound of the formula:

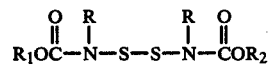

wherein:
R is alkyl having from 1 to 4 carbon atoms;
$R_1$ and $R_2$ are different and are naphthyl, tetrahydronaphthyl, dihydrobenzofuranyl, benzofuranyl, benzodioxanyl, methylenedioxyphenyl, benzothienyl or indanyl all of which may be either unsubstituted or substituted with one or more alkyl groups; or either unsubstituted or substituted phenyl, wherein the permissible substituents are one or more alkyl, alkenyl, alkynyl, alkoxycarbonylamino, alkoxy, alkynyloxy, phenoxy, alkylsulfinyl, alkylsulfonyl, alkylthio, alkenylthio, dialkylaminoalkyleneamino, alkynylthio, alkylthioalkyl, alkylsulfinylalkyl, alkylsulfonylalkyl, amino, alkylamino, dialkylamino, trihalomethyl, halo, nitro, cyano, cycloalkyl, formamidino, 2-dioxanyl, 2-dioxalanyl, 2-dithiolanyl, 2-oxathiolanyl or dicyanoethenylene;
with the proviso that $R_1$ and $R_2$ substituents individually may not include more than eight aliphatic carbon atoms.

11. A composition according to claim 10 wherein R is methyl.

12. A composition according to claim 10 wherein $R_1$ and $R_2$ are different and are naphthyl, tetrahydronaphthyl, methylenedioxyphenyl, dihydrobenzofuranyl substituted with one or more alkyl, dihydrobenzofuranyl or either unsubstituted or substituted phenyl wherein the permissible substituents are one or more alkyl, alkoxy, alkylthio, alkylsulfinyl, alkylsulfonyl, alkynyloxy, 2-(1,3-dithiolan-2-yl) or dialkylamino.

13. A composition according to claim 10 wherein $R_1$ and $R_2$ are different and are dihydrobenzofuranyl or dihydrobenzofuranyl substituted with one or more alkyl, naphthyl or phenyl substituted with one or more alkyl or dialkylamino groups.

14. A composition according to claim 10 wherein:
R is methyl;
$R_1$ and $R_2$ are different and are naphthyl, tetrahydronaphthyl, methylenedioxyphenyl, dihydrobenzofuranyl, dihydrobenzofuranyl substituted with one or more alkyl groups; or either unsubstituted or substituted phenyl wherein the permissible substituents are one or more alkyl, alkylthio, alkylsulfinyl, alkoxy, alkylsulfonyl, alkynyloxy, 2-(1,3-dithiolan-2-yl) or dialkylamino.

15. A composition according to claim 11 wherein $R_1$ and $R_2$ are different and are dihydrobenzofuranyl, dihydrobenzofuranyl substituted with one or more alkyl groups, naphthyl or phenyl substituted with one or more alkyl or dialkylamino groups.

16. A composition according to claim 10 wherein the active toxicant is N-[2,2-Dimethyl-2,3-dihydro-7-benzofuranylmethylcarbamate] N-[1-Naphthylmethylcarbamate]disulfide.

17. A composition according to claim 10 wherein the active toxicant is N-[3,5-Dimethylphenylmethylcarbamate] 2,2-Dimethyl-2,[3-dihydro-7-benzofuranylmethylcarbamate]disulfide.

18. A composition according to claim 10 wherein the active toxicant is N-[3-Dimethylaminophenylmethylcarbamate] N-[2,2-Dimethyl-2,3-dihydro-7-benzofuranylmethylcarbamate]disulfide.

19. A method of controlling insects and mites which comprises subjecting them to an insecitcidally and miticidally effective amount of a compound of the formula:

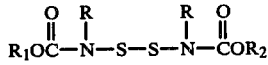

R is alkyl having from 1 to 4 carbon atoms;
$R_1$ and $R_2$ are different and are naphthyl, tetrahydronaphthyl, dihydrobenzofuranyl, benzofuranyl, benzodioxanyl, methylenedioxyphenyl, benzodioxalanyl, benzothienyl or indanyl all of which may be either unsubstituted or substituted with one or more alkyl groups; or either substituted or unsubstituted phenyl wherein the permissible substituents are one or more alkyl, alkenyl, alkynyl, alkoxycarbonylamino, alkoxy, alkynloxy, phenoxy, alkylsulfinyl, alkylsulfinyl, alkylthio, alkenylthio, dialkylaminoalkyleneamino, alkynylthio, alkylthioalkyl, alkylsulfinylalkyl, alkylsulfonylalkyl, amino, alkylamino, dialkylamino, trihalomethyl, halo, nitro, cyano, cycloalkyl, formamidino, 2-dioxanyl, 2-dioxolanyl, 2-dithiolanyl, 2-oxathiolanyl or dicyanoethenylene;
with the proviso that $R_1$ and $R_2$ substituents individually may not include more than eight aliphatic carbon atoms.

20. A method according to claim 19 wherein R is methyl.

21. A method according to claim 19 wherein $R_1$ and $R_2$ are different and are naphthyl, tetrahydronaphthyl, methylenedioxyphenyl, dihydrobenzofuranyl substituted with one or more alkyl, dihydrobenzofuranyl or either unsubstituted or substituted phenyl wherein the permissible substituents are one or more alkyl, alkylthio, alkylsulfinyl, alkylsulfonyl, alkynloxy, 2-(1,3-dithiolan-2-yl) or dialkylamino.

22. A method according to claim 19 wherein $R_1$ and $R_2$ are different and are dihydrobenzofuranyl, dihydrobenzofuranyl substituted with one or more alkyl, naphthyl or phenyl substituted with one or more alkyl or dialkylamino groups.

23. A method according to claim 19 wherein;
R is methyl;
$R_1$ and $R_2$ are different and are individually naphthyl, tetrahydronaphthyl, dihydrobenzofuranyl, benzofuranyl, benzodioxanyl, methylenedioxyphenyl, dihydrobenzofuranyl, substituted with one or more alkyl groups; or either substituted or unsubstituted phenyl wherein the permissible substituents are one or more alkyl, alkynyloxy, alkylsulfinyl, alkylsulfonyl, alkylthio, dialkylamino or 2-dithiolanyl group.

24. A method according to claim 19 wherein said compound is N[2,2-Dimethyl-2,3-dihydro-7-benzofuranylmethylcarbamate] N-[1-Naphthylmethylcarbamate] disulfide.

25. A method according to claim 19 wherein said compound is N-[3,5-Dimethylphenylmethylcarbamate] [2,2-Dimethyl-2,3-dihydro-7-benzofuranylmethylcarbamate] disulfide.

26. A method according to claim 19 wherein said compound is N-[3-Dimethylaminophenylmethylcarbamate] N-[2,2-Dimethyl-2,3-dihydro-7-benzofuranylmethylcarbamate] disulfide.

* * * * *

UNITED STATES PATENT AND TRADEMARK OFFICE
CERTIFICATE OF CORRECTION

PATENT NO. : 4,166,864
DATED : September 4, 1979
INVENTOR(S) : Themistocles D. J. D'Silva It is certified that error appears in the above-identified patent and that said Letters Patent are hereby corrected as shown below:

Column 6, line 33, "methylmethyl" should read --methylcarbamate--.

Signed and Sealed this

Twenty-fifth Day of March 1980

[SEAL]

Attest:

SIDNEY A. DIAMOND

Attesting Officer

Commissioner of Patents and Trademarks